"""

US008597419B2

(12) United States Patent  
Betts

(10) Patent No.: US 8,597,419 B2  
(45) Date of Patent: Dec. 3, 2013

(54) PRESERVATIVE COMPOSITIONS FOR WOOD AND LIKE MATERIALS

(75) Inventor: John A. Betts, Haslemere (GB)

(73) Assignee: Genics Inc., Acheson (CA)

(*) Notice: Subject to any disclaimer, the term of this patent is extended or adjusted under 35 U.S.C. 154(b) by 795 days.

(21) Appl. No.: 12/523,723

(22) PCT Filed: Jan. 17, 2008

(86) PCT No.: PCT/CA2008/000076
§ 371 (c)(1),
(2), (4) Date: Jul. 17, 2009

(87) PCT Pub. No.: WO2008/086604
PCT Pub. Date: Jul. 24, 2008

(65) Prior Publication Data
US 2010/0062166 A1    Mar. 11, 2010

(30) Foreign Application Priority Data
Jan. 17, 2007 (GB) .................................. 0700857.6

(51) Int. Cl.
| C09D 5/14 | (2006.01) |
| C09D 5/16 | (2006.01) |
| A01N 59/14 | (2006.01) |
| A01N 59/16 | (2006.01) |
| A01N 59/20 | (2006.01) |

(52) U.S. Cl.
USPC .................. 106/15.05; 106/18.11; 106/18.13; 106/18.26; 106/18.3; 106/18.27; 424/630; 424/647; 424/657; 424/658; 424/660; 428/541; 427/181

(58) Field of Classification Search
USPC ................. 428/541; 106/15.05, 18.11, 18.13, 106/18.26, 18.27, 18.3; 424/630, 647, 657, 424/658, 660; 427/181
See application file for complete search history.

(56) References Cited

U.S. PATENT DOCUMENTS

| 3,007,844 | A |   | 11/1961 | Schulz |
| 4,289,680 | A |   | 9/1981 | Kimura |
| 4,292,382 | A |   | 9/1981 | Lecerf |
| 4,439,572 | A |   | 3/1984 | Kindrick |
| 4,622,248 | A |   | 11/1986 | Leach |
| 4,643,860 | A |   | 2/1987 | Knudson |
| 4,661,157 | A |   | 4/1987 | Beauford |
| 4,857,322 | A | * | 8/1989 | Goettsche et al. ............. 424/633 |
| 4,879,083 | A |   | 11/1989 | Knudson |
| 4,911,988 | A |   | 3/1990 | Cass |
| 4,929,454 | A |   | 5/1990 | Findlay |
| 5,078,912 | A |   | 1/1992 | Goettsche |
| 5,084,280 | A |   | 1/1992 | West |
| 5,160,527 | A | * | 11/1992 | Law et al. ...................... 504/156 |
| 5,186,947 | A |   | 2/1993 | Goettsche |
| 5,187,194 | A |   | 2/1993 | Goettsche |
| 5,194,323 | A |   | 3/1993 | Savoy |
| 5,207,823 | A |   | 5/1993 | Shiozawa |
| 5,224,315 | A |   | 7/1993 | Winter, IV |
| 5,304,237 | A |   | 4/1994 | Barth |
| 5,338,791 | A |   | 8/1994 | Chaplin |
| 5,342,438 | A |   | 8/1994 | West |
| 5,426,121 | A |   | 6/1995 | Bell |
| 5,444,093 | A |   | 8/1995 | Goettsche |
| 5,478,563 | A |   | 12/1995 | Erami |
| 5,478,598 | A |   | 12/1995 | Shiozawa |
| 5,527,384 | A | * | 6/1996 | Williams et al. ........... 106/18.32 |
| 5,549,739 | A |   | 8/1996 | Inoue |
| 5,612,142 | A | * | 3/1997 | Lewis ........................... 428/528 |
| 5,634,967 | A | * | 6/1997 | Williams et al. ........... 106/18.32 |
| 5,635,217 | A |   | 6/1997 | Goettsche |
| 5,652,023 | A |   | 7/1997 | Bergervoet |
| 5,763,338 | A |   | 6/1998 | Sean |
| 5,824,370 | A |   | 10/1998 | Bergervoet |
| 5,846,305 | A |   | 12/1998 | Payzant |
| 5,874,025 | A |   | 2/1999 | Heuer |
| 5,906,828 | A |   | 5/1999 | Cima |

(Continued)

FOREIGN PATENT DOCUMENTS

| CA | 1164641 A | 4/1984 |
| CA | 2114644 C | 2/1993 |

(Continued)

OTHER PUBLICATIONS

Official Action from the Patent Office of the Russian Federation mailed Dec. 13, 2011, issued in corresponding Russian Application No. 2009131059/04(043434), filed Aug. 14, 2009, 8 pages.

Findlay, W.P.K., et al., "Boron Compounds for the Preservation of Timber Against Fungi and Insects," paper presented at the German Wood Research Association 6th Wood Protection Congress, Hamburg, Germany, Jul. 1959, 8 pages.

Freel, D., et al., "The Effect of Ethylene Glycol and Sodium Borate Solutions on the Adhesion of Epoxy to White Oak and White Pine Samples," Proceedings from the Third Conference on the Technical Aspects of the Preservation of Historic Vessels, San Francisco, Apr. 20-23, 1997, <http://www.maritime.org/conf/conf-reynolds-mat2.htm> [retrieved Dec. 19, 1997], Version 1.01, Jul. 7, 1997, 4 pages.

(Continued)

*Primary Examiner* — Joseph D Anthony
(74) *Attorney, Agent, or Firm* — Christensen O'Connor Johnson Kindness PLLC

(57) ABSTRACT

Disclosed are compositions and processes for the preservation of porous materials, particularly porous fibrous materials, such as wood, wood composites, other processed wood materials, paper, board, card, textiles, rope, cordage and leather. Also for horticultural and agricultural application to plants or growing media prevent the growth and spread of fungal and other disease. The compositions contain salts of one or more preservative metals and carboxylic acids having one or a plurality of hydroxyl groups rendered soluble by means of complex formation with boric acid or a water soluble salt thereof. Application of the compositions of this invention to the porous organic material may be by any means used with conventional preservative solutions, for example soaking, spraying, brushing and vacuum or pressure application or other contact of the solution with the material to be treated.

34 Claims, No Drawings

(56) References Cited

U.S. PATENT DOCUMENTS

| | | | |
|---|---|---|---|
| 5,916,356 A * | 6/1999 | Williams et al. | 106/18.32 |
| 5,972,266 A | 10/1999 | Fookes | |
| 5,997,971 A | 12/1999 | Wall | |
| 6,001,279 A | 12/1999 | Payzant | |
| 6,045,818 A | 4/2000 | Cima | |
| RE36,798 E * | 8/2000 | Williams et al. | 106/18.32 |
| 6,113,989 A | 9/2000 | Sinko | |
| 6,168,870 B1 | 1/2001 | Wall | |
| 6,172,117 B1 | 1/2001 | Bell | |
| 6,235,403 B1 | 5/2001 | Vinden | |
| 6,306,202 B1 * | 10/2001 | West | 106/18.3 |
| 6,352,583 B1 | 3/2002 | Goettsche | |
| 6,441,016 B2 | 8/2002 | Goettsche | |
| 6,896,908 B2 * | 5/2005 | Lloyd et al. | 424/635 |
| 7,160,606 B2 | 1/2007 | Wall | |
| 7,238,654 B2 * | 7/2007 | Hodge et al. | 510/199 |
| 2002/0146465 A1 * | 10/2002 | Lloyd et al. | 424/660 |
| 2003/0161825 A1 | 8/2003 | West | |
| 2005/0252408 A1 * | 11/2005 | Richardson et al. | 106/15.05 |
| 2005/0255251 A1 * | 11/2005 | Hodge et al. | 427/397 |
| 2006/0086284 A1 * | 4/2006 | Zhang et al. | 106/15.05 |
| 2009/0011214 A1 * | 1/2009 | Wang | 428/305.5 |
| 2009/0123505 A1 * | 5/2009 | Richardson et al. | 424/405 |

FOREIGN PATENT DOCUMENTS

| | | |
|---|---|---|
| CA | 1339375 C | 8/1997 |
| CA | 2178873 A1 | 12/1997 |
| CA | 2240216 A1 | 12/1999 |
| DE | 4036778 A1 | 5/1992 |
| EP | 0450568 A2 | 10/1991 |
| EP | 0 953 634 A1 | 11/1999 |
| PL | 147633 A1 | 7/1989 |
| RU | 190547 A1 | 12/1966 |
| SU | 190547 A | 12/1966 |
| WO | 86/07081 A1 | 12/1986 |
| WO | 96/23636 A1 | 8/1996 |
| WO | 99/43476 A1 | 9/1999 |
| WO | 03/024230 A1 | 3/2003 |
| WO | 03/025303 A1 | 3/2003 |
| WO | 2006/039753 A1 | 4/2006 |

OTHER PUBLICATIONS

International Search Report mailed May 30, 2008, in corresponding International Application No. PCT/CA2008/000076, filed Jan. 17, 2008.

Rand, T.G., "An Assessment of Mold Contamination Problems in Atlantic Canada Schools: Mold Burdens, Amplifying Sites and Benefits of Proactive School Inspection Policies," in Johanning, E. (ed.), "Bioaerosols, Fungi and Mycotoxins: Health Effects, Assessment, Prevention and Control (Third International Conference on Fungi, Mycotoxins and Bioaerosols, Saratoga Springs, N.Y., Sep. 23-25, 1998)," Mount Sinai Press, New York, 1998, pp. 581-592.

Richardson, H.W., "Copper Compounds," Encyclopedia of Chemical Technology, 4th ed., Wiley, 1993, vol. 7, pp. 505-520.

Sheard, L., "Evaluation of Boracol Rh and Impel Boron Rods: A Literature Review," Danish Technological Institute, Taastrup, Denmark, Jun. 12, 1990, 11 pages.

Singh, A.K., et al., "Evaluation of Fungicides for the Management of Taphrina Leaf Blotch of Turmeric (*Curcuma longa* L.)," Journal of Spices and Aromatic Crops 9(1):69-71, 2000.

Williams, L.H., and T.L. Amburgey, "Integrated Protection Against Lyctid Beetle Infestations. IV. Resistance of Boron-Treated Wood (*Virola* spp.) to Insect and Fungal Attack," Forest Products Journal 37(2):10-17, Feb. 1987.

Decision on Grant mailed Aug. 15, 2012, issued in corresponding Russian Application No. 2009131059, filed Jan. 17, 2008, 6 pages.

Extended European Search Report mailed Mar. 14, 2013, issued in corresponding European Application No. 08 706 224.6, filed Jan. 17, 2008, 5 pages.

Canadian Examination Report mailed Jul. 18, 2013, issued in corresponding Canadian Application No. 2,676,011, filed Jul. 20, 2009, 3 pages.

* cited by examiner

PRESERVATIVE COMPOSITIONS FOR WOOD AND LIKE MATERIALS

FIELD OF THE INVENTION

This invention relates to compositions containing complexes of salts of preservative metals with organic hydroxy acids and water soluble boron compounds. The complexes are soluble in water, in aqueous solutions of water soluble boron compounds which may be the same or different to those forming the complex and also soluble in certain organic solvents such as glycols, and in glycol solutions of glycol soluble boron compounds which may be the same or different to those forming the complex. The boron compounds impart additional preservative properties to the compositions.

The invention further relates to a process of utilizing such compositions for the preservation of porous materials, particularly porous fibrous materials, such as wood, wood composites, other processed wood materials, paper, board, card, textiles, rope, cordage and leather. These materials are prone to natural spoilage by attack by insects, fungi, moulds, bacteria and other micro-organisms.

The invention yet further relates to a process for protecting seeds and growing plants from fungal, insect, mould and bacterial attack.

BACKGROUND TO THE INVENTION

Compounds of cobalt, iron, manganese, nickel and, more particularly, copper and zinc (hereinafter collectively referred to as "preservative metals") are established preservatives for organic materials to prevent spoilage, decay and attack by pests. Such compounds, particularly those of copper, also have applications as agricultural and horticultural pesticides.

In order to apply the preservative metal compound to the porous materials in a manner suitable for it to act as a preservative, it is desirable to dissolve the compound in a carrier liquid which is capable of penetrating into the porous material.

Boron compounds in the form of boron oxide, boric acid and borate salts have a more recent history as wood preservatives, insecticides, fungicides and molluscicides replacing more toxic and environmentally undesirable materials such as chromates, arsenates, phenolic and organo-halogen pesticides, particularly poly-halogenated aromatic and cyclic compounds.

Boric acid (orthoboric acid and metaboric acid), borate salts, exemplified by borax (sodium tetraborate) and DOT (disodium octaborate tetrahydrate), are nowadays very widely used as they are effective, have low toxicity to higher life forms, have a small environmental impact at the concentrations normally used and are of relatively low cost.

To facilitate preservative activity against a wide range of spoilage organisms, it is advantageous to use more than one preservative agent. The blending of borates with one of the more usual salts of a preservative metal such as the sulfate, nitrate, chloride or acetate results in the formation of the insoluble borate salt of the preservative metal. Whilst these borate salts may have some of the desired enhanced preservative properties they are of very low solubility and are thus difficult to apply into the body of the substrate and thus have a limited action. There is thus a need for a method of combining the active borate ion and preservative metals whilst maintaining solubility in water and/or commonly used solvents.

In order to formulate useful combinations of preservative metals compatible with borate compounds, prior art has been mainly concerned with the formation and use of ammine and amine complexes of the preservative metals. These complexes have a number of disadvantages including a foul, often overpowering odor and toxicity. This has been partially overcome by the use of alkanolamines but these can introduce other problems. The release of odorous, potentially toxic vapors of ammine and amine complexes gives rise to unpleasant working conditions for operatives and requires the provision of extraction equipment or an enclosed working space. The release of ammonia and amines to the atmosphere on a large scale causes pollution and has an adverse effect on the environment.

There is thus a further need for water and glycol soluble preservative metal/borate combinations without the disadvantages described.

SUMMARY OF THE INVENTION

It is an object of the present invention to provide a composition suitable for use as a preservative for porous materials, particularly porous fibrous materials, such as wood, wood composites and other processed wood materials, textiles, ropes, cordage, paper, card and leather or as an agricultural or horticultural fungicide in the form of a powder, a granular solid, an aqueous, a glycolic or an aqueous-glycolic solution containing compounds of preservative metals and carboxylic acids having one or a plurality of hydroxyl groups rendered soluble by means of complex formation with boric acid or a water soluble salt thereof.

It is a further object of the invention to provide a process for the treatment of a porous organic material, particularly wood, by applying to the material a solution of the composition of this invention or a solid, preferably powder or granular form of the composition of this invention incorporated into porous organic materials such as laminates, fiberboard, plywood and the like during manufacture.

It is a still further object of the invention to provide a process for the protection of seeds and plants from pest attack by applying to the plant the aqueous solution of the compositions of this invention.

Thus, the present invention comprises:
(a) a compound of a preservative metal preferably selected from the group consisting of copper, zinc, cobalt, iron, manganese and nickel;
(b) an organic acid in an amount at least sufficient to form a salt of the preservative metal selected from the group consisting of aliphatic, aromatic, alicyclic or heterocyclic carboxylic acids containing two or more carbon atoms per molecule, one or a plurality of carboxyl groups per molecule and one or a plurality of hydroxyl groups per molecule; and
(c) a boron compound selected from the group consisting of boric oxide, boric acid, borate salts, boronic salts, boronic esters and mixtures thereof, the amount of boron compound being at least sufficient to form a complex with, and solubilize, said salt resulting from the reaction of (a) and (b).

The composition as defined in (a), (b), and (c) above can be offered
(i) in liquid concentrate form for application as such, for dilution in water or other suitable solvent or incorporation into other preservative products.
(ii) in dilute ready to use form for application as such or incorporation into processed products.
(iii) as a pre-reacted complex in solid form for the preparation of a concentrated aqueous solution for addition to other preservative preparations, for further dilution with water for application as is, or as a dilute ready to use preservative solution.

(iv) as a pre-reacted complex in powder or granular form for addition to wood composites and similar materials during manufacture.

(v) as a physical mixture or separate components in solid form for the in situ preparation of a solution for addition to other preservative preparations, for further dilution with water for application as is, or as a dilute ready to use preservative solution.

The preservative solutions as described above may be used for the preservation of porous organic materials, such as wood, wood composites and other processed wood materials, textiles, ropes, cordage, paper, card and leather by conventional processes such as immersion, brushing, spraying, vacuum application, pressure application, combined vacuum/pressure application and the like.

The preservative solutions as described above also have applications in agriculture and horticulture for protecting seeds and growing plants from pest attack and for application to compost and other growing media to protect against pest attack.

DETAILED DESCRIPTION OF THE INVENTION

The preservative metal in compound (a) of this invention is preferably copper, zinc, cobalt, iron, manganese or nickel, more preferably copper, zinc or cobalt and most preferably copper. In situations where the color of the preservative of this invention and, in turn, the color of the item treated with the preservative is of concern, zinc is the preferred preservative metal.

Component (b) of the compositions is a carboxylic acid with one or a plurality of carboxyl groups per molecule and one or a plurality of hydroxyl groups per molecule. Representative and non-limiting examples of acids within the meaning of this invention are:

(i) Aliphatic monocarboxylic acids with one hydroxyl group: glycolic acid(hydroxyacetic acid), lactic acid(2-hydroxypropionic acid).

(ii) Aliphatic monocarboxylic acids with a plurality of hydroxyl groups: gluconic acid(pentahydroxyhexanoic acid), glucoheptonic acid(glucomonocarboxylic acid).

(iii) Aliphatic dicarboxylic acids with one hydroxyl group per molecule: malic acid(hydroxybutanedioic acid).

(iv) Aliphatic dicarboxylic acids with two hydroxyl groups: tartaric acid(2,3-dihydroxybutanedioic acid) and its isomers.

(v) Aliphatic dicarboxylic acids with four hydroxyl groups: glucaric acid(tetra-hydroxyhexanedioic acid).

(vi) Aliphatic tricarboxylic acids with one hydroxyl group: citric acid(2-hydroxypropane-1,2,3-tricarboxylic acid).

A number of other organic carboxylic acids fulfill the requirements of the definition for this invention but they are generally laboratory curiosities of little practical or commercial application.

Combinations of two or more organic acids and/or salts of such acids may be used in carrying out this invention and it is acceptable to use any known commercially available product. Isomers of these acids or mixtures of isomers are also within the scope of this invention The salts of the preservative metals defined in (a) above and organic acids as defined in (b) above (hereinafter collectively referred to as "preservative salts") may be articles of commerce. Alternatively, the preservative salts may be prepared extemporaneously by conventional chemical methods known by those skilled in the art.

Component (c) of the compositions of this invention is a water soluble boron compound in the form of boric oxide, boric acid, borate salts, boronic salts and boronic esters. It is known that boric acid and borate salts form complexes with organic compounds that contain a plurality of hydroxyl groups. We have discovered that the borate complexes of the preservative salts are highly soluble in water thus providing a means of utilizing the preservative metal in the presence of the borate ion, facilitating the formation of concentrated solutions. Furthermore, we have unexpectedly discovered that solutions of the borate complexes of preservative salts are stable in the presence of excess borate ions, thus the preservative salt-borate complexes can be added to other borate containing preservative solutions which may be already in widespread use.

The solvent carrier for the solutions of the compositions of this invention is, for reasons of economy and convenience, water. Some advantage may be gained by the use of a glycol solvent either alone or in combination with an aqueous solvent. Glycol solvents of particular merit for this application include ethylene glycol(ethane-1,2-diol), diethylene glycol (2,2'-oxybisethanol), triethylene glycol(2,2'-ethyenedioxybis[ethanol]), polyethylene glycols of molecular weights with the range 200-6000, propylene glycol(propane-1,2-diol), dipropylene glycol(oxybispropanol), water soluble polypropylene glycols, trimethylene glycol(propane-1,3-diol), glycerine(propane-1,2,3-triol), hexamethylene glycol (1,6-hexanediol), pentamethylene glycol(1,5-pentanediol), 1,3-butylene glycol(1,3-butanediol), 2,3-butylene glycol(2,3-butanediol), 2-ethoxyethanol, 2-(2-ethoxyethoxyethanol), butoxyethanol, 2-(2-butoxyethoxy)ethanol, 1-methoxy-2-propanol, 1-ethoxy-2-propanol, methoxy-propoxypropanol, ethoxypropoxypropanol and related solvents.

The penetration of the composition of this invention into the deeper parts of the porous organic material, particularly porous fibrous material, such as wood, wood composites and other processed wood materials, textiles, ropes, cordage and leather may be enhanced by the inclusion of a detergent or surfactant into the composition of this invention. Non-limiting examples of surfactants suitable for this application include ethylene glycol/propylene glycol copolymer surfactants, polyethylene glycol ester surfactants, polyethylene ether surfactants, other non-ionic surfactants, anionic surfactants, cationic surfactants, zwitterionic surfactants, silicone glycol surfactants, fluorinated surfactants.

This invention thus further consists in a process for the treatment of a porous organic material, particularly porous fibrous material, such as wood, wood composites and other processed wood materials, textiles, ropes, cordage and leather by applying to the material an aqueous, a glycol or aqueous/glycol solution of the invention or a composition containing said solution.

This invention still further consists of a process for the treatment during the processing of porous organic materials, particularly wood composites and other processed wood materials, by incorporating the compositions of this invention, preferably in powder or granular form, into the porous organic materials during manufacture.

Application of the compositions of this invention to the porous organic material may be by any means used with conventional preservative solutions, for example soaking, spraying, brushing, and vacuum or pressure application or other contact of the solution with the material to be treated. Treatment of wood is preferably by a pressure method and commercial units and systems are available. Application of the solution by simple soaking or steeping requires sufficient time for the solution to penetrate and, in the case of timber of large bulk, this can be prolonged. Unseasoned timber may be treated by diffusion or by any other well known process that allows diffusion into wet wood.

Although the solutions of this invention are of particular value in the treatment of solid timber and, for this reason, the treatment of solid timber has been described in detail above, they may also, by adoption of suitable application techniques, be used for the treatment of wood chips, fiber board, particle board, plywood or other fibrous materials, including paper pulp, paper, board, card, textiles, rope cordage and leather and means for treating these materials are well known to those skilled in the art.

The aqueous solutions of the compositions of this invention, particularly those containing copper as the preservative metal, are also valuable for the treatment of seeds or growing plants in agriculture, horticulture or home garden use to prevent the growth and spread of fungal and other plant or growing media disease. The solutions may be applied by any method used for the application of known fungicidal solutions, but are most preferably applied by spraying. Application of the compositions of this invention in solid form as powder or granules to compost and other growing media may also be made The invention is further illustrated by the following non-limiting Examples:

EXAMPLE 1

About 500 g of copper sulfate pentahydrate was dissolved in a suitable quantity of hot water. A stoichiometric quantity of a solution of potassium sodium tartrate was then mixed into the hot copper sulfate solution with stirring. Copper tartrate precipitated from the mixture as a pale blue powder. After cooling, the precipitate was washed several times with water to remove sulfate ions and vacuum filtered to leave a paste containing 60-70% copper tartrate trihydrate.

The solids content of the paste was determined by drying a sample to constant weight at 110° C.

A quantity of the paste equivalent to 420 g copper tartrate trihydrate (=100 g copper) was mixed with 200 g borax (sodium tetraborate decahydrate) and sufficient water to make 1,000 g. The mixture was stirred and heated to facilitate the formation of the borate/tartrate complex. The resulting composition contained about 10% of copper and was a clear, deep blue, viscous solution miscible with water and solutions of borate salts.

EXAMPLE 2

About 500 g zinc sulfate heptahydrate was dissolved in a suitable quantity of hot water. A stoichiometric quantity of a solution of potassium sodium tartrate was then mixed into the hot zinc sulfate solution with stirring. Zinc tartrate precipitated from the mixture as a white powder. After cooling, the precipitate was washed several times with water to remove sulfate ions and vacuum filtered to leave a paste containing 60-70% zinc tartrate dihydrate.

The solids content of the paste was determined by drying a sample to constant weight at 110° C.

A quantity of the paste equivalent to 420 g zinc tartrate dihydrate (=100 g zinc) was mixed with 200 g borax (sodium tetraborate decahydrate) and sufficient water to make 1,000 g. The mixture was stirred and heated to facilitate the formation of the borate/tartrate complex. The resulting composition contained about 10% of zinc was a clear, colorless, viscous solution miscible with water and solutions of borate salts.

EXAMPLE 3

500 g copper gluconate was mixed with 200 g borax decahydrate and 300 g water. The mixture was stirred and heated to about 60° C. to dissolve the solids and facilitate the reaction to form the borate/gluconate complex. The resulting composition contained about 7% copper and was a clear, bluish-green, viscous liquid miscible with water and solutions of borate salts.

EXAMPLE 4

500 g zinc gluconate was mixed with 200 g borax decahydrate and 300 g water. The mixture was stirred and heated to about 60° C. to form the borate/gluconate complex. The resulting composition contained about 7% zinc and was a clear, colorless, viscous liquid miscible with water and solutions of borate salts.

EXAMPLE 5

360 g copper tartrate tetrahydrate in powder form was suspended in 440 g water and 200 g borax decahydrate added. The mixture was stirred and heated to about 80° C. and allowed to react to form the borate/tartrate complex. Water lost by evaporation was replaced. The resulting composition contained about 8% copper and was a clear, deep blue, viscous solution miscible with water and solutions of borate salts.

EXAMPLE 6

500 g copper gluconate was mixed with 250 g borax decahydrate and 100 g water. The mixture was stirred and heated to about 60° C. to form the gluconate/borate complex. The solids dissolved to form a clear, very dark green, viscous mass. The reaction product was spread on to a flexible polyethylene sheet and the excess moisture was allowed to evaporate. The resultant product was a dark green, brittle, glass-like solid easily crushed to form granules or powder. The product was very soluble in water and solutions of borate salts, forming a blue-green, clear to slightly hazy solution. The solid contained about 9% copper.

EXAMPLE 7

500 g zinc gluconate was mixed with 250 g borax decahydrate and 100 g water. The mixture was stirred and heated to about 60° C. to form the gluconate/borate complex. The solids dissolved to form a clear, colorless, viscous mass. The reaction product was spread on to a flexible polyethylene sheet and the excess moisture was allowed to evaporate. The resultant product was a colorless, brittle, glass-like solid easily crushed to form granules or powder. The product was very soluble in water and solutions of borate salts, forming a colorless, clear to slightly hazy solution. The solid contained about 9% zinc.

EXAMPLE 8

About 100 g copper carbonate of commerce (equivalent to 50 g Cu) was slowly added to about 625 g of warm gluconic acid (50% solution of commerce). When the evolution of carbon dioxide had ceased and the copper carbonate dissolved, 200 g borax decahydrate was added and the solution made up to 1,000 g with water. The resulting composition contained about 5% copper and was a clear to slightly hazy, bluish-green, viscous liquid miscible with water and solutions of borate salts.

In addition, various known additives may be combined with the preservative compositions formulated according to this invention without substantially affecting the preservative capability of this invention. For example, other preservative compounds and compositions may be added to the compositions of this invention. Coloring agents, waxes, resins, aqueous solutions, various emulsions and suspensions and other ingredients may be added to the compositions of this invention where such additional properties are desirable.

The compositions of this invention may also be used to treat growing media such as compost, living plants and seeds to prevent and/or treat fungal, insect, mould and bacterial attack. For this purpose the treatment solution would preferably be applied by spraying methods but the solutions may be applied by any method commonly used to apply known pesticides to growing media, seed and plants, agricultural and horticultural crops. For the treatment of growing media, the compositions of this invention in solid form, as demonstrated in Examples 6 and 7, may be preferred.

From the foregoing, it will be appreciated that, although specific embodiments of this invention have been described herein for the purposes of illustration, various modifications may be made without deviating from the spirit and scope of the invention. Accordingly, this invention is not limited except as by the appended Claims.

I claim:

1. A composition for use as a preservative, wherein the composition is synthesized from:
   (a) a metal salt formed from:
      (i) an acid having an anion selected from gluconate, tartrate, or carbonate;
      (ii) a metal selected from cobalt, iron, manganese, nickel, copper, and zinc; and
      (iii) a solvent; and
   (b) at least one water soluble boron-containing compound that forms a complex with the metal salt.

2. The composition of claim 1, wherein the metal is copper, zinc, or copper and zinc.

3. The composition of claim 1, wherein the solvent is an aqueous solvent or a glycol-based solvent.

4. The composition of claim 3, wherein the solvent is selected from at least one of ethylene glycol(ethane-1,2-diol), diethylene glycol(2,2'-oxybisethanol), triethylene glycol(2,2'-ethyenedioxybis[ethanol]), polyethylene glycols of molecular weights with the range 200-6000, propylene glycol (propane-1,2-diol), dipropylene glycol (oxybispropanol), water soluble polypropylene glycols, trimethylene glycol (propane-1,3-diol), glycerine(propane-1,2,3-triol), hexamethylene glycol(1,6-hexanediol), pentamethylene glycol (1,5-pentanediol), 1,3-butylene glycol(1,3-butanediol), and 2,3-butylene glycol(2,3-butanediol).

5. The composition of claim 1, further comprising a surfactant.

6. The composition of claim 5, wherein the surfactant is selected from ethylene glycol/propylene glycol copolymer surfactants, polyethylene glycol ester surfactants, polyethylene ether surfactants, other non-ionic surfactants, anionic surfactants, cationic surfactants, zwitterionic surfactants, silicone glycol surfactants, and fluorinated surfactants.

7. The composition of claim 1, further comprising:
   at least one organic acid comprising at least two carbon atoms, at least one carboxylic acid functional group, and at least one hydroxyl group functional group per molecule.

8. The composition of claim 7, wherein the composition comprises complexes.

9. The composition of claim 7, wherein the organic acid is an aliphatic monocarboxylic acid, a dicarboxylic acid or a tricarboxylic acid comprising at least one hydroxyl functional group per molecule.

10. The composition of claim 9, wherein the organic acid is a monocarboxylic acid.

11. The composition of claim 9, wherein the organic acid is a dicarboxylic acid.

12. The composition of claim 9, wherein the organic acid is a tricarboxylic acid.

13. The composition of claim 7, wherein the organic acid is selected from at least one of:
   (i) glycolic(hydroxyacetic) acid or lactic(2-hydroxypropionic)acid,
   (ii) gluconic acid(pentahydroxyhexanoic acid) or glucoheptonic acid(glucose monocarboxylic acid),
   (iii) malic acid(hydroxybutanedioic acid),
   (iv) tartaric acid(2,3-dihydroxybutanedioic acid), its isomers, and half salts; or glucaric acid(tetrahydroxy-hexane-1,6-dioic acid)acid, its isomers, and half salts; or galactaric acid, its isomers, and half salts, and
   (v) citric acid(2-hydroxypropane-1,2,3-tricarboxylic acid).

14. The composition of claim 1, wherein the boron-containing compounds are selected from at least one of boron oxide, boric acid, metaboric acid, orthoboric acid, borax decahydrate, borax pentahydrate, anhydrous borax, sodium borates, potassium borates, lithium borates, ammonium borates, amine borates, and alkanolamine borates.

15. The composition of claim 14, wherein the boron-containing compounds are selected from at least one of disodium octaborate, sodium pentaborate, sodium metaborate, potassium pentaborate, ammonium biborate, and ammonium pentaborate.

16. The composition of claim 7, wherein the composition is dried to form a solid.

17. The composition of claim 16, wherein the solid is granular or powdered.

18. The composition of claim 1, further comprising a second preservative.

19. The composition of claim 18, wherein the second preservative comprises borate ion.

20. A method of utilizing a composition as a preservative, the method comprising:
   (i) selecting a metal precursor compound composed of:
      (a) an acid having an anion selected from gluconate, tartrate or carbonate; and
      (b) a metal selected from cobalt, iron, manganese, nickel, copper, and zinc;
   (ii) preparing the composition by dissolving the acid and the metal in a solvent to produce a metal salt;
   (iii) complexing the metal salt with at least one water soluble boron-containing compound to form a complex; and
   (iv) applying the complex to a substrate.

21. The method of claim 20, wherein the solvent is selected from at least one of water, ethylene glycol(ethane-1,2-diol), diethylene glycol(2,2'-oxybisethanol), triethylene glycol(2,2'-ethyenedioxybis[ethanol]), polyethylene glycols of molecular weights with the range 200-6000, propylene glycol (propane-1,2-diol), dipropylene glycol(oxybispropanol), water soluble polypropylene glycols, trimethylene glycol (propane-1,3-diol), glycerine(propane-1,2,3-triol), hexamethylene glycol(1,6-hexanediol), pentamethylene glycol(1,5-pentanediol), 1,3-butylene glycol(1,3-butanediol), and 2,3-butylene glycol(2,3-butanediol).

22. The method of claim 20, further comprising adding a surfactant.

23. The method of claim 20, wherein the composition is applied by brushing, spraying, or steeping.

24. The method claim 20, wherein the composition is applied by steeping, the method further comprising increasing or decreasing pressure, or both increasing and decreasing pressure during steeping.

25. The method of claim 20, wherein the substrate is selected from seeds, plant material, growth medium or porous fibrous materials, the porous fibrous materials selected from wood, processed wood materials, paper, cardboard, textiles, rope, cordage, or leather.

26. The method of claim 20, further comprising selecting at least one organic acid comprising at least two carbon atoms, at least one carboxylic acid functional group, and at least one hydroxyl group functional group per molecule.

27. The method of claim 26, further comprising selecting the at least one organic acid from an aliphatic monocarboxylic acid, a dicarboxylic acid or a tricarboxylic acid comprising at least one hydroxyl functional group per molecule or a compound for the production of an aliphatic monocarboxylic acid, a dicarboxylic acid or a tricarboxylic acid comprising at least one hydroxyl functional group per molecule.

28. The method of claim 27, further comprising selecting at least one of:
(i) glycolic (hydroxyacetic) acid or lactic(2-hydroxypropionic)acid,
(ii) gluconic acid(pentahydroxyhexanoic acid) or glucoheptonic acid(glucose monocarboxylic acid),
(iii) malic acid(hydroxybutanedioic acid),
(iv) tartaric acid(2,3-dihydroxybutanedioic acid), its isomers, and half salts; or glucaric acid(tetrahydroxy-hexane-1,6-dioic acid)acid, its isomers, and half salts; or galactaric acid, its isomers, and half salts, and
(v) citric acid(2-hydroxypropane-1,2,3-tricarboxylic acid).

29. The method of claim 26, wherein complexing the metal salt with at least one water soluble boron-containing compound to form a complex comprises complexing the metal salt with at least one of boron oxide, boric acid, metaboric acid, orthoboric acid, borax decahydrate, borax pentahydrate, anhydrous borax, sodium borates, potassium borates, lithium borates, ammonium borates, amine borates, or alkanolamine borates.

30. The method of claim 26, further comprising drying the complex to form a solid.

31. The method of claim 30, further comprising powdering or granulating the solid.

32. The method of claim 20, further comprising adding a second preservative.

33. The method of claim 32, wherein the second preservative comprises borate ion.

34. A method of preparing a composition for use as a preservative, the method comprising:
(i) selecting:
(a) an acid having an anion selected from gluconate, tartrate, or carbonate;
(b) a metal selected from cobalt, iron, manganese, nickel, copper, and zinc; and
(c) at least one organic acid comprising at least two carbon atoms, at least one carboxylic acid functional group, and at least one hydroxyl group functional group per molecule;
(ii) preparing a metal salt by dissolving the acid having an anion and the metal in a solvent;
(iii) dissolving the metal salt in the organic acid; and
(iv) complexing the metal salt by the addition of a boron-containing compound to prepare a complex.

* * * * *

UNITED STATES PATENT AND TRADEMARK OFFICE
CERTIFICATE OF CORRECTION

| | |
|---|---|
| PATENT NO. | : 8,597,419 B2 |
| APPLICATION NO. | : 12/523723 |
| DATED | : December 3, 2013 |
| INVENTOR(S) | : J. A. Betts |

Page 1 of 1

It is certified that error appears in the above-identified patent and that said Letters Patent is hereby corrected as shown below:

In the Claims:

| COLUMN | LINE | |
|---|---|---|
| 9 | 11 | "The method claim" should read |
| (Claim 24, | line 1) | --The method of claim-- |

Signed and Sealed this
Twelfth Day of August, 2014

Michelle K. Lee
*Deputy Director of the United States Patent and Trademark Office*